(12) United States Patent
Bergnes et al.

(10) Patent No.: US 6,753,428 B2
(45) Date of Patent: Jun. 22, 2004

(54) PROCESS FOR THE RACEMIZATION OF CHIRAL QUINAZOLINONES

(75) Inventors: Gustave Bergnes, Pacifica, CA (US); Bing Yao, Hayward, CA (US); David Morgans, Jr., Los Altos, CA (US); Whitney W. Smith, El Cerrito, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 10/300,967

(22) Filed: Nov. 20, 2002

(65) Prior Publication Data

US 2003/0166933 A1 Sep. 4, 2003

Related U.S. Application Data

(60) Provisional application No. 60/332,148, filed on Nov. 20, 2001.

(51) Int. Cl.[7] .............................................. C07D 239/80
(52) U.S. Cl. ...................................... 544/283; 544/284
(58) Field of Search .................................. 544/283, 284

(56) References Cited

U.S. PATENT DOCUMENTS

| 3,320,124 | A | 5/1967 | Waletzky et al. |
|---|---|---|---|
| 3,322,756 | A | 5/1967 | Ruschig et al. |
| 3,723,432 | A | 3/1973 | Ott |
| 3,740,442 | A | 6/1973 | Ott et al. |
| 3,925,548 | A | 12/1975 | Oh |
| 4,729,996 | A | 3/1988 | Wright et al. |
| 4,808,590 | A | 2/1989 | Higa et al. |
| 4,857,530 | A | 8/1989 | Berman et al. |
| 4,866,084 | A | 9/1989 | Gunasekera et al. |
| 4,970,226 | A | 11/1990 | Sun et al. |
| 4,981,856 | A | 1/1991 | Hughes |
| 4,992,550 | A | 2/1991 | Hughes |
| 5,037,829 | A | 8/1991 | Freyne et al. |
| 5,081,124 | A | 1/1992 | Hughes |
| 5,147,875 | A | 9/1992 | Coates et al. |
| 5,187,167 | A | 2/1993 | Hughes |
| 5,204,354 | A | 4/1993 | Chakravarty et al. |
| 5,280,027 | A | 1/1994 | Andrew et al. |
| 5,316,906 | A | 5/1994 | Haugland et al. |
| 5,430,148 | A | 7/1995 | Webber et al. |
| 5,449,678 | A | 9/1995 | Pines et al. |
| 5,470,878 | A | 11/1995 | Michnick et al. |
| 5,561,133 | A | 10/1996 | Bisset et al. |
| 5,574,057 | A | 11/1996 | Ireland et al. |
| 5,707,992 | A | 1/1998 | Webber et al. |
| 5,714,493 | A | 2/1998 | Myers et al. |
| 5,747,498 | A | 5/1998 | Schnur et al. |
| 5,753,664 | A | 5/1998 | Aono et al. |
| 5,756,450 | A | 5/1998 | Hahn et al. |
| 5,756,502 | A | 5/1998 | Padia et al. |
| 5,756,510 | A | 5/1998 | Griffin et al. |
| 5,770,595 | A | 6/1998 | Klein et al. |
| 5,773,476 | A | 6/1998 | Chen et al. |
| 5,777,115 | A | 7/1998 | Leigh et al. |
| 5,780,476 | A | 7/1998 | Underiner et al. |
| 5,783,577 | A | 7/1998 | Houghten et al. |
| 5,789,427 | A | 8/1998 | Chen et al. |
| 5,795,898 | A | 8/1998 | Brown et al. |
| 5,801,181 | A | 9/1998 | Michnick et al. |
| 5,801,182 | A | 9/1998 | Klein et al. |
| 5,804,584 | A | 9/1998 | Underiner et al. |
| 5,807,861 | A | 9/1998 | Klein et al. |
| 5,807,862 | A | 9/1998 | Klein et al. |
| 5,811,429 | A | 9/1998 | Connell et al. |
| 5,817,662 | A | 10/1998 | Klein et al. |
| 5,837,703 | A | 11/1998 | Kumar et al. |
| 5,852,024 | A | 12/1998 | Pines et al. |
| 5,859,018 | A | 1/1999 | Brown et al. |
| 5,869,665 | A | 2/1999 | Padia et al. |
| 5,885,996 | A | 3/1999 | Webber et al. |
| 5,891,879 | A | 4/1999 | Nagler et al. |
| 5,922,866 | A | 7/1999 | Miyata et al. |
| 5,929,081 | A | 7/1999 | Brown et al. |
| 6,545,005 | B1 | 4/2003 | Price et al. |
| 6,559,160 | B1 | 5/2003 | Schall et al. |
| 6,613,798 | B1 | 9/2003 | Porter et al. |

FOREIGN PATENT DOCUMENTS

| EP | 0 056 637 | 7/1982 |
|---|---|---|
| EP | 0286813 | 10/1988 |
| EP | 884316 A1 | 3/1990 |
| EP | 360417 A2/3 | 3/1990 |
| EP | 0884310 A1 | 12/1998 |
| EP | 0900568 A2 | 3/1999 |
| EP | 0903344 A1 | 3/1999 |
| EP | 0056637 A1 | 7/1999 |
| GB | 2271111 A | 4/1994 |
| WO | WO 96/06616 | 3/1995 |
| WO | WO 95/24379 | 9/1995 |
| WO | WO 94/21259 | 9/1999 |
| WO | WO 00/07017 | 2/2000 |
| WO | WO 97/10221 | 3/2000 |
| WO | WO 01/74344 A2 | 10/2000 |
| WO | WO 01/030768 | 5/2001 |

OTHER PUBLICATIONS

CHEMCATS Copyright 2000 ACS, 1998:596123 CHEMCATS, Maybridge, Apr. 3, 2000, DP 01489, N2–(3–pyridylmethyl)–4–oxo–3,4–dihydroquinazoline–2–carboxamide, 190437–46–8, Chemical Library.

Q Kozhevnikov, V. and Pilat, N.V. [4–Quinazolinones. II. 2–(Aminomethyl)–2–aryl–4– quinazolinones.] (Russian) Tr Perm Sel–Khoz Inst (79):66–72, 1971 CA 78:16128.

Gupta, C.M. et al. Drugs acting on the central nervous system. Synthesis of substituted quinazolones and quinazolines and triazepino and triazocinoquinazolones. J Med Chem 11 :392.395, 1968.

(List continued on next page.)

Primary Examiner—John M. Ford
(74) Attorney, Agent, or Firm—Swiss Law Group

(57) ABSTRACT

Racemates are obtained from one of the enantiomers, or an enantiomerically enriched mixture, of an optically active quinazolinone derivative by reaction of the compound with an alkali alkoxide of a primary alcohol and isolation of the racemate.

12 Claims, 4 Drawing Sheets

OTHER PUBLICATIONS

Saari. W .S. et al. Synthesis and evaluation of 2–pyridinone derivatives as HIV–1–specific reverse transcriptase inhibitors. 2. Analogues of 2–aminopyridin–2('H)–one. J Med Chem 35:3792–3802, 1992.

Farghaly, A.M. et al. Non–steroidal antiinflammatory agents. III: Synthesis of pyrazole derivatives of 4(3H)–quinazolinones. Alexandria J Pharm Sci 4(1):52.56, 1990.

Dymek. W. et al. 2–Chloromethyl–6–methylquinazoline–4 and its transformations. Diss Pharm et Pharmacol 20(1):29–34, 1968.

Pattanaik, J.M. et al. Synthesis and fungicidal activity of 3–aryl–2–4–aryl thazol–2'– ylaminomethyl) quinazol–4(3H)–ones. Indian J Chem 37B:1304–1306, 1998.

Gupta, D.P. and Shanker, K. Thiazolidinones. azetidinones and formazans of quinazolinones. Indian J Chem 26B:1197–1199, 1987.

Parasharya, P .M. and Parikh, A.R. 4–(3H)–Quinazolones part I: 2–Alkyl/arylaminomethyl–3–p–hydroxy/methoxy phenyl–4(3H)–quinazolones. J Inst Chemists (India) 64: 184–185, 1992.

Parasharya, P.M. et al. 4(3H)–Quinazolones: 2–N–aryvalkyl–amino–methyvethyl–3–p– hydroxyphenyll p–anisyl/p–aryaminoacyloxyphenyl/p–N–arylcarbamoyl-methoxyphenyl–4(3H)–quinazolones. J Inst Chemists (India) 64:238–24, 1992.

Matthews. N. et al. Structure–activity relationships of phenothiazines in inhibiting lymphocyte motility as determined by a novel flow cytometric assay. Biochem Pharmacol 50(7):1053–1061, 1995.

List of Purchased Compounds 10/00.

A.K. Debnath, "Structure Based Identification of Small Molecule Antiviral Compounds", Journal of Medicinal Chemistry, vol. 42, No. 17, Aug. 1999, pp. 3203–3209.

Bocakei, "Two Antithrombotic Quinazolone Derivatives," Acta. Cryst. (1995) C51:723–723.

Monika, "Synthesis of Potential CCK Antagonist Quinazolone," Acta. Pharm. Hungarica, pp. 175–181, 1995.

Ager et al., "Synthesis and Central Nervous System Activity of Quinazolones Related to 2–Methyl–3–(o–tolyl)–4(3H)–quinazolone (Methaqualone)", Jrnl of Med. Chem., (1977) vol. 20, No. 3, pp. 379–386.

AU–A–12617/88, Australian patent application "New N–substd. Omega–aminoacid derives.—which are selective inhibitors of human plasma renin" (1988).

Tiwari et al., "Synthesis and CNS Activity of 2–Aryl–3(3', 4'–Dihydroxyphenylethyl) 6–8–substituted–4 (3H)–Quinazolinones", Indian Jrnl of Pharm. Sciences, Mar./Apr. 1978, pp. 40–43.

Rao et al., "Synthesis and Biological Activities of Certain Derivatives of 3–Aryl–4(3H)–quinazolinones. Part–II", J. Indian Chem. Soc., vol. LXII, Mar. 1985, pp. 234–237.

Registry file compounds from unspecified chemical libraries.

Rao, A. Devender et al., "Synthesis and Biological Activities of Certain Derivatives of 3–Aryl–4(3H)–quinazolinones. Part–II", 1985, *Journal of Indian Chemical Society*, vol. 62, pp. 234–237.

Singh, Buddha Deo and Chaudhury, D. N., "4–Quinazolones–II Synthesis of Some Imidazo $[1,_{5-a}]$ Quinazolones", 1969, *Journal of Indian Chemical Society*, vol. 46, pp. 21–25.

*Chemical Abstracts*, vol. 96, Abstract No. 142790p (1982).

Step 1:  Butyryl chloride / DMF

Step 2:  Acetic anhydride

Step 3:  Benzylamine (CHCl$_3$) (Ethylene glycol NaOH)

Step 4:  Br$_2$/AcOH NaOAc

Step 5:  N,N-Dimethyl ethylendiamine EtOH

Step 6:  4-FC$_6$H$_4$-COCl

R-isomer   S-isomer

PROCESS FOR THE RACEMIZATION OF CHIRAL QUINAZOLINONES

CROSS REFERENCE TO RELATED APPLICATIONS

This application claims priority under 35 U.S.C. §119(e) to U.S. Ser. No. 60/332,148, filed Nov. 20, 2001, which is incorporated by reference in its entirety for all purposes.

FIELD OF THE INVENTION

This invention relates to a process for racemizing one of the enantiomers, or an enantiomerically enriched mixture, of an optically active compound. This invention more specifically relates to racemization of quinazolinone derivatives.

BACKGROUND OF THE INVENTION

Interest in the medicinal chemistry of quinazoline derivatives was stimulated in the early 1950's with the elucidation of the structure of a quinazoline alkaloid, 3-[β-keto-γ-(3-hydroxy-2-piperidyl)-propyl]-4-quinazolone, from an Asian plant known for its antimalarial properties. In a quest to find additional antimalarial agents, various substituted quinazolines have been synthesized. Of particular import was the synthesis of the derivative 2-methyl-3-o-tolyl-4-(3H)-quinazolinone. This compound, known by the name methaqualone, though ineffective against protozoa, was found to be a potent hypnotic.

Since the introduction of methaqualone and its discovery as a hypnotic, the pharmacological activity of quinazolinones and related compounds has been investigated. Quinazolinones and derivatives thereof are now known to have a wide variety of biological properties including hypnotic, sedative, analgesic, anticonvulsant, antitussive and anti-inflammatory activities.

Quinazolinones are among a growing number of therapeutic agents used to treat cell proliferative disorders, including cancer. For example, PCT WO 01/30768, which is incorporated herein by reference in its entirety, describes a pharmaceutical composition containing quinazolinone derivatives which are inhibitors of the mitotic kinesin KSP and are useful in the treatment of cellular proliferative diseases, for example cancer, hyperplasias, restenosis, cardiac hypertrophy, immune disorders and inflammation. Certain of the compounds described therein have the following formula:

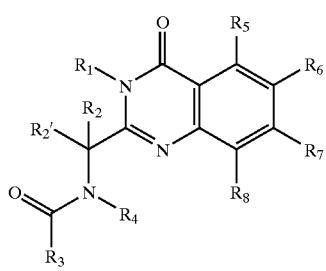

Formula I(a)

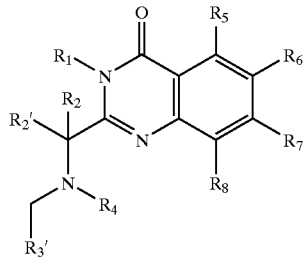

Formula I(d)

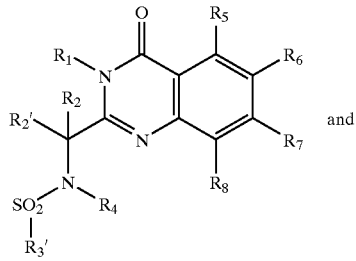

Formula I(b)

and

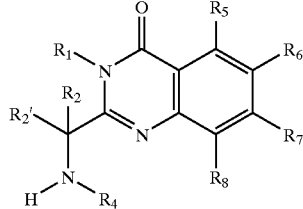

Formula I(c)

wherein $R_1$ is chosen from hydrogen, alkyl, aryl, aralkyl, heteroaryl, heteroaralkyl, substituted alkyl, substituted aryl, substituted aralkyl, substituted heteroaryl, and substituted heteroaralkyl;

$R_2$ and $R_2'$ are independently chosen from hydrogen, alkyl, oxaalkyl, aryl, aralkyl, heteroaryl, heteroaralkyl, substituted alkyl, substituted aryl, substituted aralkyl, substituted heteroaryl, and substituted heteroaralkyl; or $R_2$ and $R_2'$ taken together form a 3- to 7-membered ring;

$R_3$ is chosen from hydrogen, alkyl, aryl, aralkyl, heteroaryl, heteroaralkyl, substituted alkyl, substituted aryl, substituted aralkyl, substituted heteroaryl, substituted heteroaralkyl, oxaalkyl, oxaaralkyl, substituted oxaaralkyl, $R_{15}O-$ and $R_{15}-NH-$;

$R_{3a}$ is chosen from hydrogen, alkyl, aryl, alkylaryl, heteroaryl, alkylheteroaryl, substituted alkyl, substituted aryl, substituted alkylaryl, substituted heteroaryl, substituted alkylheteroaryl and $R_{15}-NH-$;

$R_{3b}$ is chosen from alkyl, aryl, alkylaryl, heteroaryl, alkylheteroaryl, substituted alkyl, substituted aryl, substituted alkylaryl, substituted heteroaryl, and substituted alkylheteroaryl;

$R_4$ is chosen from hydrogen, alkyl, aryl, aralkyl, heteroaryl, heteroaralkyl, substituted alkyl, substituted aryl, substituted aralkyl, substituted heteroaryl, substituted heteroaralkyl, and $R_{16}$-alkylene-;

$R_5$, $R_6$, $R_7$ and $R_8$ are independently chosen from hydrogen, alkyl, alkoxy, halogen, fluoroalkyl, nitro, dialkylamino, alkylsulfonyl, alkylsulfonamido, sulfonamidoalkyl, sulfonamidoaryl, alkylthio, carboxyalkyl, carboxamido, aminocarbonyl, aryl and heteroaryl;

$R_{15}$ is chosen from alkyl, aryl, aralkyl, heteroaryl, heteroaralkyl, substituted alkyl, substituted aryl, substituted aralkyl, substituted heteroaryl, and substituted heteroaralkyl; and $R_{16}$ is chosen from alkoxy, amino, alkylamino, dialkylamino, N-heterocyclyl and substituted N-heterocyclyl.

These quinazolinone derivatives have an asymmetric carbon atom (i.e., the stereogenic center to which $R_2$ and $R_{2'}$ are attached) that may exist as a racemic mixture of these compounds, i.e., a mixture of both the (+) and (−) or dextro and levo rotary forms. These compounds can be produced as racemates and administered in this form. However, it is known that the physiological utility of racemic mixtures often is focused on one enantiomer, the other having either little or no effect or even diminishing the effect of the active enantiomer.

A generic synthetic scheme for the preparation of quinazolinone compounds of Formula I(a)–(d) above is described in PCT WO 01/30768 and is shown in FIGS. 1 and 2. An asymmetric synthesis of the quinazolinone compounds of Formula I using optically active reagents is shown in FIG. 3. Disposal of the undesired enantiomer of an intermediate is not environmentally or economically desirable. Thus an efficient method of converting the inactive or undesirable enantiomer into the other usable, desirable enantiomer is a commercially important objective. This invention makes it possible to achieve this objective.

The references discussed herein are provided solely for their disclosure prior to the filing date of the present application and are each incorporated herein by reference. Nothing herein is to be construed as an admission that the inventors are not entitled to antedate such disclosure by virtue of prior invention.

SUMMARY OF THE INVENTION

The present invention provides a method for racemizing one of the enantiomers, or an enantiomerically enriched mixture, of an optically active compound of the formula:

Formula II

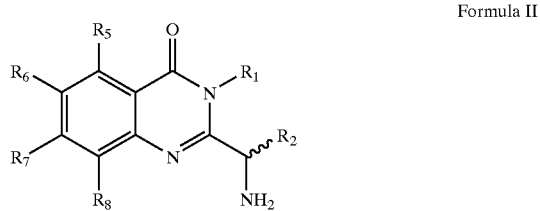

comprising:
  contacting said compound with an alkali alkoxide of a $C_1$–$C_6$ primary alcohol; and
  isolating the resulting racemic compound,
wherein
  $R_1$ is chosen from hydrogen, alkyl, aryl, aralkyl, heteroaryl, heteroaralkyl, substituted alkyl, substituted aryl, substituted aralkyl, substituted heteroaryl, and substituted heteroaralkyl;
  $R_2$ is alkyl, oxaalkyl, aryl, aralkyl, heteroaryl, heteroaralkyl, substituted alkyl, substituted aryl, substituted aralkyl, substituted heteroaryl, and substituted heteroaralkyl; and
  $R_5$, $R_6$, $R_7$ and $R_8$ are independently chosen from hydrogen, alkyl, alkoxy, halogen, fluoroalkyl, nitro, dialkylamino, alkylsulfonyl, alkylsulfonamido, sulfonamidoalkyl, sulfonamidoaryl, alkylthio, carboxyalkyl, carboxamido, aminocarbonyl, aryl and heteroaryl.

The process is characterized in that one of the enantiomers, or an enantiomerically enriched mixture, of enantiomers is contacted with an alkali metal alkoxide of a primary alcohol. Preferably, the reaction mixture comprises the primary alcohol from which the alkali metal alkoxide was derived. The racemic compounds can then be isolated by conventional methods.

The alkali metal alkoxide of a primary alcohol will generally be derived from a primary aliphatic alcohol with 1–6 C-atoms, preferably methanol or ethanol, and more preferably, ethanol. Preferably, the reaction is carried out under reflux temperature.

BRIEF DESCRIPTION OF THE DRAWINGS

This invention will be better understood by reference to the following drawings and description, in which the same reference numerals are used to identify like components.

DESCRIPTION OF THE PREFERRED EMBODIMENT

General

Figure 1:
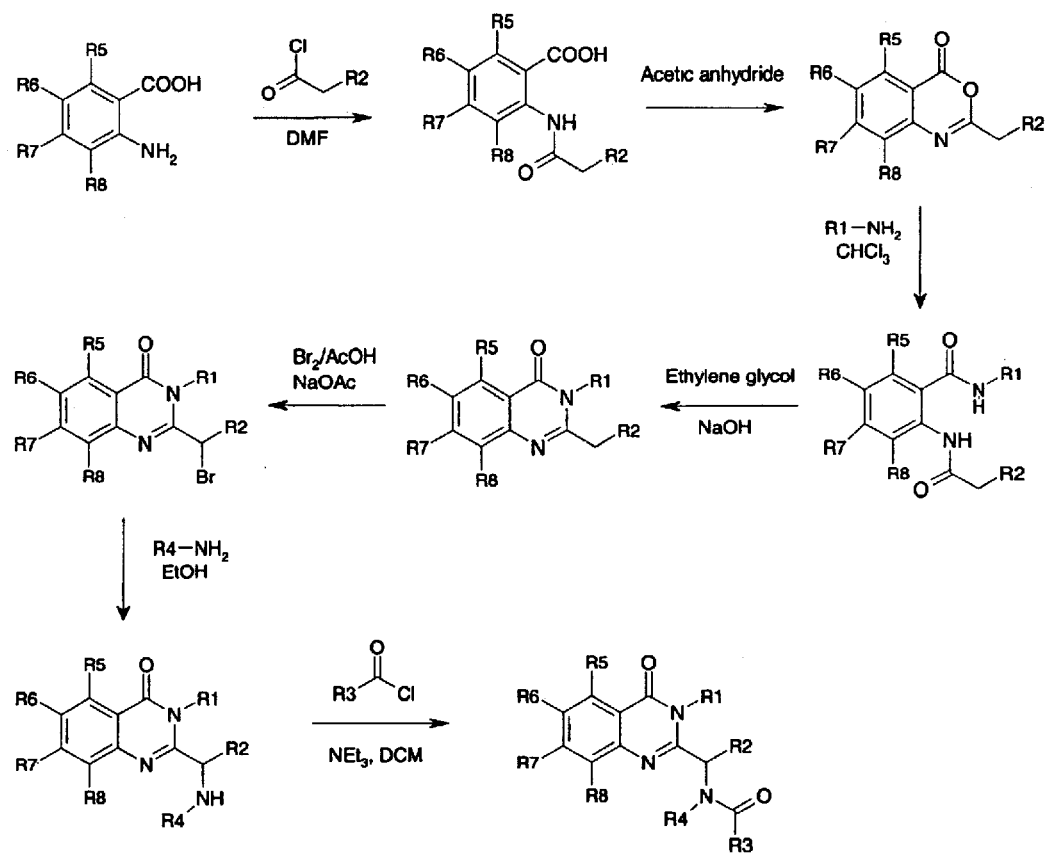
FIG. 1 depicts a generic synthetic scheme to make quinazolinone derivatives of Formula I.

Before the present methods are described, it is understood that this invention is not limited to the particular methodology, protocols, and reagents described, as these may vary. It is also to he understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described.

Alkyl is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s-and t-butyl and the like. Preferred alkyl groups are those of $C_{20}$ or below. More preferred alkyl groups are those of $C_{13}$ or below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, and the like. In this application, alkyl refers to alkanyl, alkenyl and alkynyl residues; it is intended to include cyclohexylmethyl, vinyl, allyl, isoprenyl and the like. Alkylene refers to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH$ ($C_6H_{13}$)—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S. The aromatic 6- to 14-membered carbocyclic rings include, e.g., benzene, naphthalene, indane, tetralin, and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Aralkyl refers to a residue in which an aryl moiety is attached to the parent structure via an alkyl residue. Examples are benzyl, phenethyl, phenylvinyl, phenylallyl and the like. Oxaalkyl and oxaaralkyl refer to alkyl and aralkyl residues in which one or more methylenes have been replaced by oxygen. Examples of oxaalkyl and oxaaralkyl residues are ethoxyethoxyethyl (3,6-dioxaoctyl), benzyloxymethyl and phenoxymethyl; in general, glycol ethers, such as polyethyleneglycol, are intended to be encompassed by this group.

Heteroaralkyl refers to a residue in which a heteroaryl moiety is attached to the parent structure via an alkyl residue. Examples include furanylmethyl, pyridinylmethyl, pyrimidinylethyl and the like.

Heterocycle means a cycloalkyl or aryl residue in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

Substituted alkyl, aryl and heteroaryl refer to alkyl, aryl or heteroaryl wherein H atoms are replaced with alkyl, halogen, hydroxy, alkoxy, alkylenedioxy (e.g. methylenedioxy) fluoroalkyl, carboxy (—COOH), carboalkoxy (i.e. acyloxy RCOO—), carboxyalkyl (—COOR), carboxamido, sulfonamidoalkyl, sulfonamidoaryl, aminocarbonyl, benzyloxycarbonylamino (CBZ-amino), cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy. For the purposes of the present invention, substituted alkyl also includes oxaalkyl residues, i.e. alkyl residues in which one or more carbons has been replaced by oxygen.

Halogen refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

Starting Materials

In a preferred embodiment, an enantiomer, or an enantiomerically enriched mixture, of an optically active compound will have a formula:

Formula II

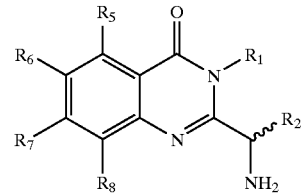

wherein $R_1$ is chosen from hydrogen, alkyl, aryl, aralkyl, heteroaryl, heteroaralkyl, substituted alkyl, substituted aryl, substituted aralkyl, substituted heteroaryl, and substituted heteroaralkyl;

$R_2$ is alkyl, oxaalkyl, aryl, aralkyl, heteroaryl, heteroaralkyl, substituted alkyl, substituted aryl, substituted aralkyl, substituted heteroaryl, and substituted heteroaralkyl; and $R_5$, $R_6$, $R_7$ and $R_8$ are independently chosen from hydrogen, alkyl, alkoxy, halogen, fluoroalkyl, nitro, cyano, dialkylamino, alkylsulfonyl, alkylsulfonamido, sulfonamidoalkyl, sulfonamidoaryl, alkylthio, carboxyalkyl, carboxamido, aminocarbonyl, aryl and heteroaryl. See, PCT WO 01/30768.

These compounds contain one or more asymmetric centers (e.g. the carbon to which $R_2$ is attached) and may thus give rise to enantiomers, diastereomers, and other stereoisomeric forms that may be defined, in terms of absolute stereochemistry, as (R)- or (S)-. The quinazolinones of Formula II which are enriched in one optical isomer may be used in the present invention irrespective of the degree of enantiomeric excess of a specific optical isomer contained therein. Thus, the starting material of the racemization method described herein may be enriched with the R-configuration or the S-configuration. Preferably, it will be enriched with the S-isomer.

Preferably, $R_1$ is selected from hydrogen, alkyl, aryl, substituted alkyl, substituted aryl, heteroaryl, substituted heteroaryl, aralkyl, substituted aralkyl, and substituted heteroaralkyl.

In a more preferred embodiment $R_1$ is selected from hydrogen, lower alkyl, substituted lower alkyl, aryl, substituted aryl, aralkyl and substituted aralkyl. In a most preferred embodiment $R_1$ is chosen from hydrogen, ethyl, propyl, methoxyethyl, naphthyl, phenyl, bromophenyl, chlorophenyl, methoxyphenyl, ethoxyphenyl, tolyl, dimethylphenyl, chorofluorophenyl, methylchlorophenyl, ethylphenyl, phenethyl, benzyl, chlorobenzyl, methylbenzyl, methoxybenzyl, tetrahydrofuranylmethyl and (ethoxycarbonyl)ethyl.

In a preferred embodiment $R_2$ is alkyl or substituted alkyl. In a most preferred embodiment $R_2$ is chosen from methyl, ethyl, propyl, methylthioethyl, aminobutyl, (CBZ) aminobutyl, cyclohexylmethyl, benzyloxymethyl, methylsulfinylethyl, methylsulfinylmethyl, hydroxymethyl, benzyl and indolylmethyl.

Preferably, $R_5$, $R_6$, $R_7$ and $R_8$ are independently chosen from hydrogen, halogen, methyl, cyano, and trifluoromethyl. More preferably, $R_5$ is hydrogen or halogen; $R_6$ is hydrogen, methyl, or halogen; $R_7$ is hydrogen, halogen, lower alkyl, substituted lower alkyl, lower alkoxy, or cyano; and/or $R_8$ is hydrogen or halogen. In another embodiment, embodiment, $R_5$, $R_6$, and $R_8$ are hydrogen. More preferably, $R_5$, $R_6$, and $R_8$ are hydrogen and $R_7$ is halogen In a particularly preferred subgenus, $R_1$ is chosen from aralkyl or substituted aralkyl; $R_2$ is lower alkyl; $R_5$ is hydrogen; $R_6$ is hydrogen; $R_7$ is halo or cyano; and $R_8$ is hydrogen; or $R_1$ is benzyl or substituted benzyl; $R_2$ is i-propyl; $R_5$ is hydrogen; $R_6$ is hydrogen; $R_7$ is chloro or cyano; and $R_8$ is hydrogen; or $R_1$ is benzyl; $R_2$ is i-propyl; $R_5$ is hydrogen; $R_6$ is hydrogen; $R_7$ is fluoro; and $R_8$ is hydrogen, or $R_1$ is benzyl; $R_2$ is i-propyl; $R_5$ is hydrogen; $R_6$ is hydrogen; $R_7$ is chloro; and $R_8$ is hydrogen; or $R_1$ is benzyl; $R_2$ is i-propyl; $R_5$ is hydrogen; $R_6$ is hydrogen; $R_7$ is cyano; and $R_8$ is hydrogen; or $R_1$ is benzyl or halobenzyl; $R_2$ is chosen from ethyl and propyl; $R_5$ is hydrogen; $R_6$ is hydrogen; $R_7$ is halo; and $R_8$ is hydrogen.

The Racemization Methods

In the racemization method of the present invention, racemization produces a racemic mixture, which can be separated by conventional means such as column chromatography, optical resolution using an optically active acid and the like.

The methods of the present invention utilize an alkali alkoxide of a $C_1$–$C_6$ primary alcohol to effect the racemization. Preferably, the alkali alkoxide will comprise a sodium or potassium alkoxide. More preferably, it will comprise sodium ethoxide.

The amount of alkali alkoxide used is not particularly limited, but is usually from about 0.01 to 10 moles, preferably 0.01 to 5 moles, more preferably 0.5 to 2 moles per mole of the quinazolinone derivative. Most preferably, equimolar amounts of the alkali alkoxide and the quinazolinone will be used.

Preferably, a $C_1$–$C_6$ primary alcohol will be used as the solvent. More preferably, the solvent will comprise the alcohol from which the alkali alkoxide was derived. Most preferably, the primary alcohol will be methanol or ethanol. Preferably, the racemization reaction will be conducted in anhydrous conditions.

The reaction mixture may comprise lesser amounts of other solvent including aromatic compounds such as benzene, toluene, ethyl benzene, xylene, and chlorobenzene; hydrocarbons such as hexane, cyclohexane, heptane and isooctane; ethers such as t-butyl methyl ether, isopropyl ether, tetrahydrofuran and dioxane, and mixtures thereof.

The concentration of starting material in the racemization reaction may be varied. In general, the reaction will be conducted at a concentration of about 0.1 to about 5 molar, more preferably at about 0.5 to about 2 molar, and most preferably at about 0.5 molar.

The racemization reaction usually will be conducted at a temperature of less than 200° C.; more preferably, at a temperature of less than 100° C.; and most preferably, at the reflux (or boiling point) temperature of the reaction mixture.

The product of the racemization reaction (i.e., the "racemates") will be less enriched in one optical isomer and thus, will have a decreased degree of enantiomeric excess as compared to the starting material. Preferably, the racemates will be present in about a 1:1 ratio.

The racemized quinazolinone derivative thus obtained by the present invention can be reused in an optical resolution process to produce the desired enantiomer of the optically active quinazolinone derivative after being subjected to a conventional procedure, for example, hydrolysis or neutralization with acidic water or the like, followed by distillation of the solvent, if necessary.

Synthesis of Compounds of Formula II

The compounds of Formula II can be prepared by following the procedures described with reference to the Reaction Scheme 1 below and by the procedures set forth in the figures and PCT WO 01/30768.

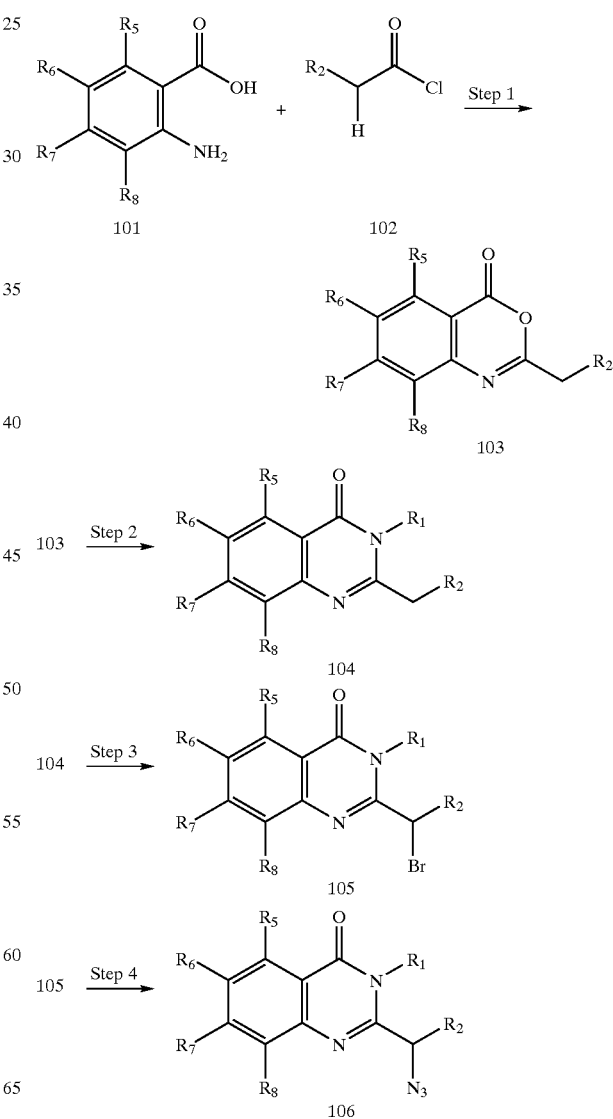

Reaction Scheme 1

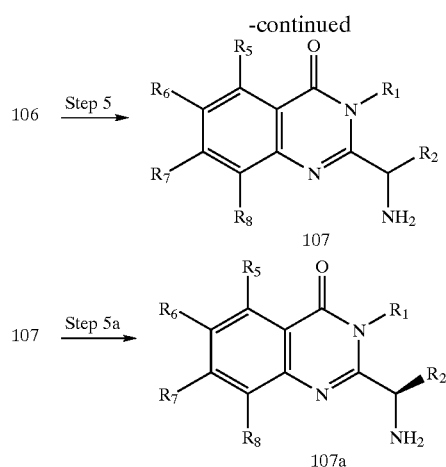

Preparation of Formula 103

Referring to Reaction Scheme 1, Step 1, to an optionally substituted benzoic acid (the compound of Formula 101) dissolved in an inert organic solvent (such as THF) in the presence of sodium bicarbonate and a dehydrating agent (such as $Na_2SO_4$) is added a slight molar excess of an optionally substituted acid chloride (the compound of Formula 102), maintaining about room temperature. Completion of the reaction is monitored, e.g., by TLC. Acetic anhydride is then added to the reaction mixture, which is heated to about 90–100° C., monitoring completion of the reaction (e.g., by TLC) followed by removal of the acetic anhydride under vacuum at about 80–100° C. The reaction mixture is cooled and the corresponding, optionally substituted benzo[d][1,3]oxazin-4-one (the compound of Formula 103) is isolated and purified.

Preparation of Formula 104

Referring to Reaction Scheme 1, Step 2, about 1.5 molar equivalents of a primary amine (such as $R_1NH_2$) and 1 molar equivalent of a compound of Formula 103 in an inert organic solvent (such as toluene) are heated to reflux. The reaction takes place over a period of 1 to 5 hours. After removal of water, ethylene glycol and sodium hydroxide are added to the reaction mixture and the temperature raised to 110–120° C. Completion of the reaction is monitored, e.g., by TLC. The corresponding, optionally substituted quinazolinone (a compound of Formula 104) is isolated and purified.

Preparation of Formula 105

Referring to Reaction Scheme 1, Step 3, a compound of Formula 104, dissolved in acetic acid and in the presence of sodium acetate, is heated to 30° C., followed by the addition (with agitation) of a slight molar excess of bromine in acetic acid over a period of 2.5 hours. Completion is monitored, e.g., by TLC; if the starting material continues to be present, temperature is increased to 50° C. until completion. The corresponding, optionally substituted quinazolinone of Formula 105 is isolated and purified.

Preparation of Formula 106

Referring to Reaction Scheme 1, Step 4, to 1.5 molar equivalents of sodium azide in an inert organic solvent (such as DMF) is slowly added 1 molar equivalent of a compound of Formula 105. The reaction takes place with agitation at a temperature of 40° C. over a period of 3 to 10 hours. Completion is monitored, e.g., by TLC. The corresponding, optionally substituted quinazolinone azide of Formula 106 is isolated and purified.

Preparation of Formula 107

Referring to Reaction Scheme 1, Step 5, to a solution of triphenylphosphine dissolved in an inert organic solvent (such as THF) is added an azide of Formula 106, portionwise over about 15 minutes. The reaction takes place with agitation, maintaining the temperature at 20° C. over a period of 5 minutes to 1 hour. The reaction mixture is acidified, solvents removed followed by conventional work up to give the hydrochloride salt of the corresponding, optionally substituted quinazolinone of Formula 107, which is isolated and purified in the usual manner. Preparation of Formula 107a In certain compounds of the invention, particular stereo-configuration can be preferred for the R2 substituent, such as the (R) isomer, which can be obtained, e.g., as illustrated in optional Step 5a of Reaction Scheme 1. An amine of Formula 107 is dissolved in an inert organic solvent (such as IPA) and warmed to 60° C. In a separate vessel, a resolving agent (such as dibenzoyl-D-tartaric acid) is dissolved, preferably in the same warm solvent, and then quickly added (with agitation) to the warm amine solution. The reaction mixture is left to crystallize by cooling to room temperature over 16 hours under continuing agitation. The desired isomer, e.g., the (R) isomer illustrated as Formula 107a, is isolated and purified in the usual manner.

Synthesis of Compounds of Formula I

The quinazolinone derivative of Formula II can be converted to compounds of Formula I(a), 1(b), I(c), or I(d) as described in the Reaction Schemes below and as shown in the figures. See, also, PCT WO 01/30768.

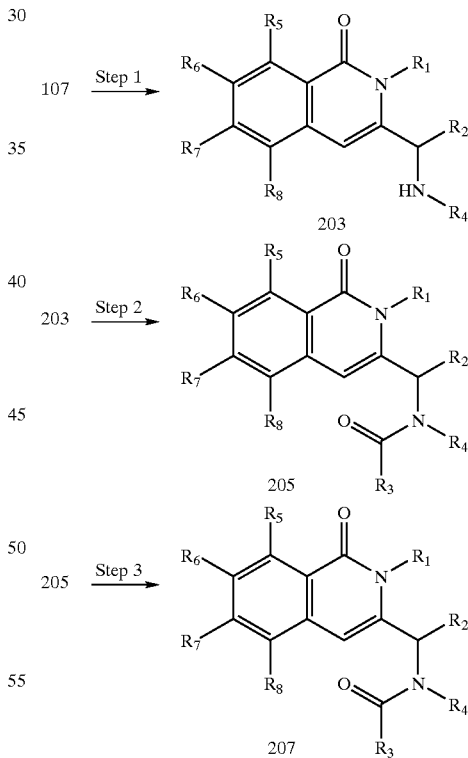

Preparation of Formula 203

Referring to Reaction Scheme 2, Step 1, to a solution of a compound of Formula 107 is added successively a slight excess (preferably about 1.2 equivalents) of an aldehyde comprising $R_{4'}$ (i.e., a compound having the formula $R_{4'}CHO$ where $R_{4'}CH_2$— is equivalent to $R_4$ and $R_4$ is as described above or is a protected precursor to such a substituent, e.g., (3-oxo-propyl)-carbamic acid tert-butyl ester) and a reducing agent such as sodium triacetoxyborohydride. The resulting mixture is stirred for several hours. The product, a compound of Formula 203 is isolated and purified.

Preparation of Formula 205

Referring to Reaction Scheme 2, Step 2, to a solution of a compound of Formula 203 and an amine base such as diisopropylethylamine in a nonpolar, aprotic solvent such as dichloromethane is added an $R_3$ acyl chloride (such as Cl—C(O)—$R_3$ where $R_3$ is as described above). The resulting solution is stirred under nitrogen at room temperature for several hours. The product, a compound of Formula 205 is isolated and purified.

Preparation of Formula 207

Optionally, any protecting groups on compounds of Formula 205 are then removed. For example, if $R_4$ comprises a protected amine wherein the protecting group is a Boc group, the Boc group can be removed by treatment of the compound of Formula 205 with an acid such as trifluoroacetic acid in a nonpolar, aprotic solvent such as dichloromethane, while maintaining the reaction at about room temperature. The reaction is monitored e.g., by TLC. Upon completion, the product, a compound of Formula 207 is isolated and purified.

Reaction Scheme 3

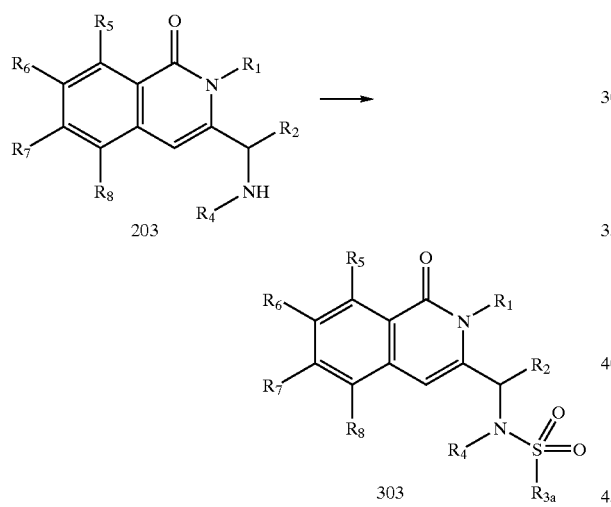

Referring to Reaction Scheme 3, to a solution of a compound of Formula 203 and an amine base such as diisopropylethylamine in a nonpolar, aprotic solvent such as dichloromethane is added a compound having the formula Cl—S(O)$_2$—$R_{3a}$ or O—(S(O)$_2$—$R_{3a}$)$_2$ where $R_{3a}$ is as described above. The resulting solution is stirred under nitrogen at room temperature for several hours. The product, a compound of Formula 303 is isolated and purified.

Reaction Scheme 4

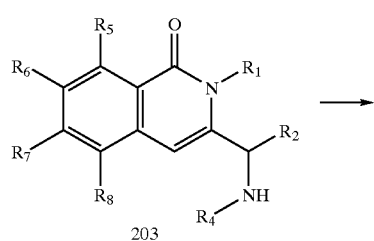

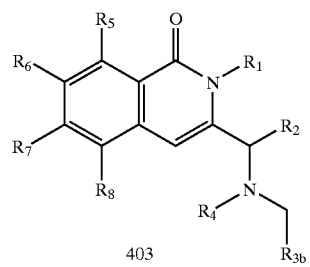

Referring to Reaction Scheme 4, to a solution of a compound of Formula 203 and an amine base such as diisopropylethylamine in a nonpolar, aprotic solvent such as dichloromethane is added a compound having the formula Cl—CH$_2$—$R_{3b}$ where $R_{3b}$ is as described above. The resulting solution is stirred under nitrogen at room temperature or with heat for several hours. The product, a compound of Formula 403 is isolated and purified.

Reaction Scheme 5

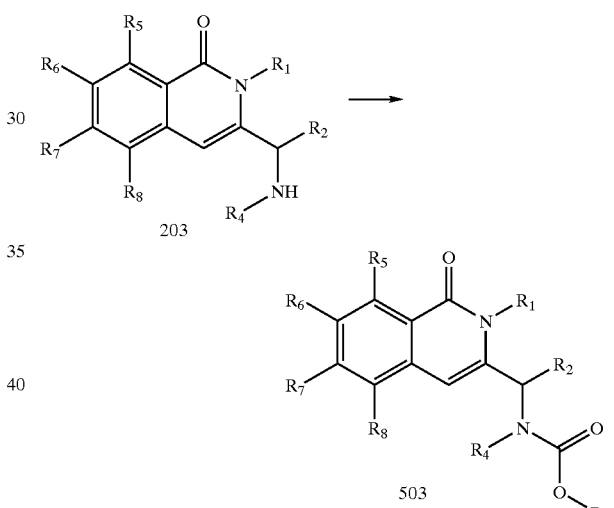

Referring to Reaction Scheme 5, a compound of Formula 203 is reacted with a slight excess of a compound of the formula $R_{15}$O(CO)Cl in the presence of a base such as triethylamine in a nonpolar, aprotic solvent such as dichloromethane. The product, a compound of Formula 503 is isolated and purified.

Reaction Scheme 6

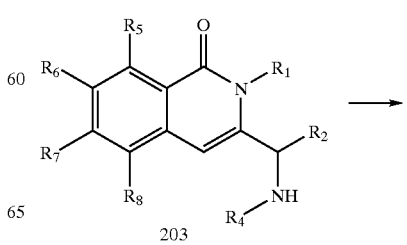

-continued

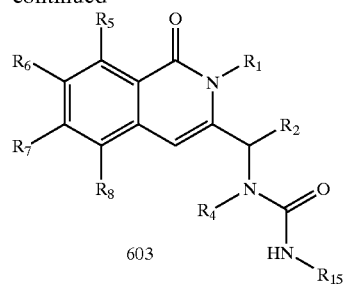

603

Referring to Reaction Scheme 6, a compound of Formula 203 is treated with a slight excess of an isocyanate $R_{15}$—N=C=O in the presence of a base, such as triethylamine, in a nonpolar, aprotic solvent, such as dichloromethane. The product, a compound of Formula 603, is isolated and purified.

EXAMPLES

Abbreviations and Definitions

The following examples are given to enable those skilled in the art to more clearly understand and to practice the present invention. They should not be considered as limiting the scope of the invention, but merely as being illustrative and representative thereof.

| The following abbreviations and terms have the indicated meanings throughout: | |
|---|---|
| Ac = | acetyl |
| Boc = | t-butyloxy carbonyl |
| Bu = | butyl |
| c- = | cyclo |
| CBZ = | carbobenzoxy = benzyloxycarbonyl |
| DBU = | diazabicyclo[5.4.0]undec-7-ene |
| DCM = | dichloromethane = methylene chloride = $CH_2Cl_2$ |
| DCE = | dichloroethylene |
| DEAD = | diethyl azodicarboxylate |
| DIC = | diisopropylcarbodiimide |
| DIEA = | N,N-diisopropylethyl amine |
| DMAP = | 4-N,N-dimethylaminopyridine |
| DMF = | N,N-dimethylformamide |
| DMSO = | dimethyl sulfoxide |
| DVB = | 1,4-divinylbenzene |
| EEDQ = | 2-ethoxy-1-ethoxycarbonyl-1,2-dihydroquinoline |
| Et = | ethyl |
| Fmoc = | 9-fluorenylmethoxycarbonyl |
| GC = | gas chromatography |
| HATU = | O-(7-Azabenzotriazol-1-yl)-1,1,3,3-tetramethyluronium hexafluorophosphate |
| HMDS = | hexamethyldisilazane |
| HOAc = | acetic acid |
| HOBt = | hydroxybenzotriazole |
| Me = | methyl |
| mesyl = | methanesulfonyl |
| MTBE = | methyl t-butyl ether |
| NMO = | N-methylmorpholine oxide |
| PEG = | polyethylene glycol |
| Ph = | phenyl |
| PhOH = | phenol |
| PfP = | pentafluorophenol |
| PPTS = | pyridinium p-toluenesulfonate |
| Py = | pyridine |
| PyBroP = | bromo-tris-pyrrolidino-phosphonium hexafluorophosphate |
| rt = | room temperature |
| sat = d = | saturated |
| s- = | secondary |
| t- = | tertiary |

| The following abbreviations and terms have the indicated meanings throughout: | |
|---|---|
| TBDMS = | t-butyldimethylsilyl |
| TES = | triethylsilane |
| TFA = | trifluoroacetic acid |
| THF = | tetrahydrofuran |
| TMOF = | trimethyl orthoformate |
| TMS = | trimethylsilyl |
| tosyl = | p-toluenesulfonyl |
| Trt = | triphenylmethyl |

Example 1

Synthesis of Compounds

Figure 2:
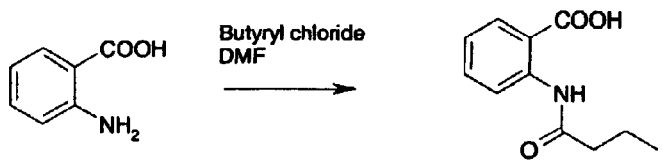
FIG. 2 depicts a synthetic route for the synthesis of quinazolinone derivative
Figure 2:
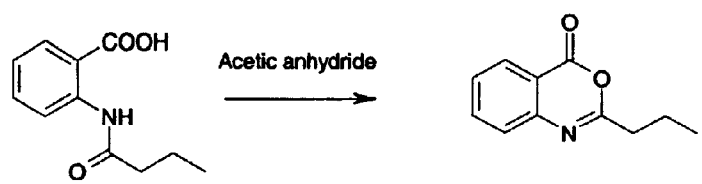
Figure 2:
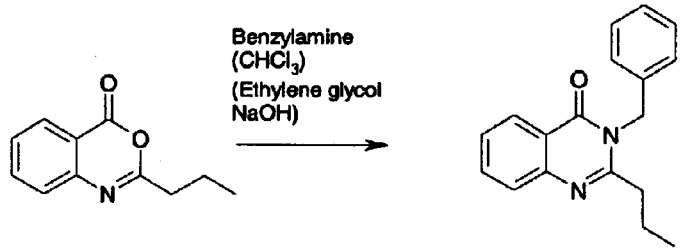
Figure 2:
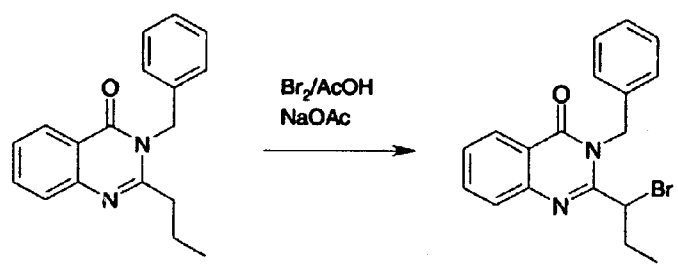
Figure 2:
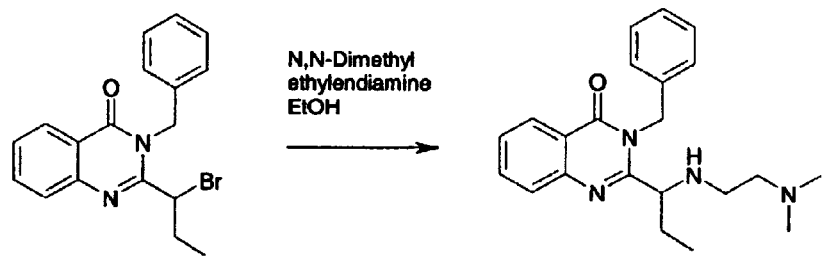
Figure 2:
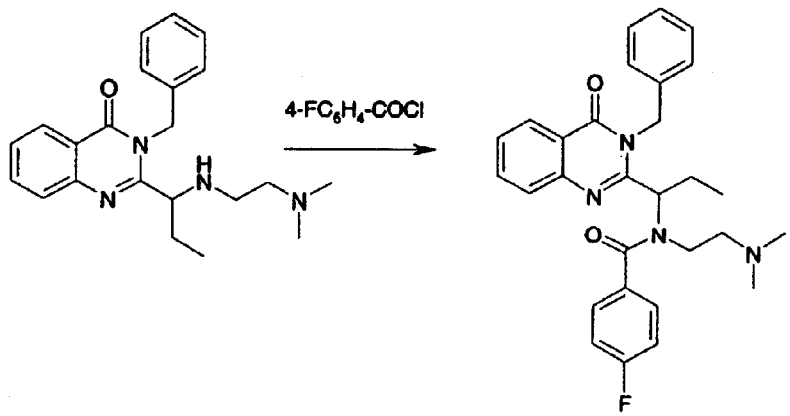

The general synthesis is shown in FIGS. 1 and 2 and is described further above.

Step 1: N-butyryl anthranilic acid.

To a three-necked, 500 mL round-bottom flask equipped with a thermometer, dropping funnel, and an efficient magnetic stir bar, was added anthranilic acid (1) (0.5 mole, 68.5 g) and dimethyl formamide (250 mL). To this solution was added butyryl chloride (0.55 mole, 57.1 mL) dropwise at such a rate that the temperature of the mixture did not rise above 40° C. The suspension was stirred vigorously at room temperature for at least an additional 3 h. The mixture was poured into water (2000 mL) and stirred for another 1 h. The precipitated product was collected by filtration, washed with cold water, and dried under reduced pressure over $P_2O_5$, yielding compound 2 (67.3 g, 65%).

Step 2: 2-Propyl-3,1-[4H]benzoxazin-4-one.

Compound 2 (51.8 g, 0.25 mole) was dissolved in acetic anhydride (180 mL) in a 500 mL round-bottom flask equipped with a magnetic stir bar, a Claisen-distillation head (with vacuum inlet) and a thermometer. The flask was placed in an oil bath and slowly heated to 170–180° C. with vigorous stirring. The acetic acid produced was slowly distilled off under atmospheric pressure. Monitoring the head temperature of the distillation unit was used to follow the progress of the transformation. The reaction mixture was then cooled to 60° C. and the excess of acetic anhydride removed by distillation under reduced pressure (ca. 20 mm Hg). The residue was afterward cooled and the product crystallized. The product was triturated with n-hexane (75 mL) and isolated by filtration to yield 2-propyl-3,1-[4H] benzoxazin-4-one (3) (29.3 g, 62%). The above procedure gave compound 3 sufficiently pure to use directly in the next step.

Step 3: 2-Propyl-3-benzylquinazolin-4-one.

Compound 3 (28.4 g, 0.15 mole) and benzylamine (17.5 mL, 0.16 mole) were refluxed in chloroform (50 ml) in a one-neck 250 mL round-bottom flask for 6 h. After complete consumption of compound 3, the chloroform was evaporated under reduced pressure. Ethylene glycol (100 mL) and NaOH pellets (0.60 g) were added to the residue and the flask equipped with a Claisen-distillation head and a magnetic stir bar. The flask was immersed in an oil bath and reheated to 130–140° C. bath temperature with vigorous stirring and maintained there for 5 h while the water produced was removed by distillation. After completion of the reaction, the clear solution was allowed to cool to room temperature and kept overnight to precipitate the product. The pH of the suspension was adjusted to 7–8 by adding 3% aq. HCl, the crystals were filtered off and washed with cold water, and then recrystallized from isopropanol (or alternatively from acetone) to provide the compound, 2-propyl-3-benzylquinazolin-4-one (compound 4) (28.0 g, 67%).

Step 4: 2-(I'-bromopropyl)-3-benzylquinazolin-4-one.

To a three-neck 250 mL round-bottom flask equipped with a thermometer, dropping funnel, and efficient magnetic stir bar was added compound 4 (27.8 g, 0.10 mole), anhydrous sodium acetate (10.0 g) and glacial acetic acid (130 mL). Bromine (16.0 g, 0.10 mole) dissolved in acetic acid (10 mL) was added dropwise to the above solution at 40° C. for 1–2 h. After addition was complete, the mixture was poured into water (1500 mL) and stirred for 1–2 h at room temperature. The precipitated product, 2-(I'-bromopropyl)-3-benzylquinazolin-4-one (5) was isolated by filtration, washed with warm water to remove traces of acetic acid, and rinsed with a small amount of isopropanol. Drying yielded compound 5 (33.0 g, 92%).

Step 5: 2-[I'-(N,N-dimethylethylenediamino)propyl]-3-benzylquinazolin-4-one.

Compound 5 (10.7 g, 0.03 mole) and N,N-dimethylethylenediamine (6.6 mL, 0.06 mole) were dissolved in abs. ethanol (60 mL) and heated at reflux for 6 h. After completion of the reaction, the solvent was evaporated under reduced pressure. The residue was dissolved in dichloromethane (150 mL) and washed with 3% aq. NaOH solution (ca. 10–20 mL). The organic layer was dried over MgSO$_4$ and evaporated to dryness under reduced pressure. The remaining oily product was purified by flash chromatography on a short silica gel pad using an eluent of CHCl$_3$—MeOH—aq.NH$_3$, 90:10:0.1, to give the desired compound (5), 2-[I'-(N,N-dimethylethylenediamino) propyl]-3-benzylquinazolin-4-one (6) (6.0 g, 55%).

Step 6: 2-[I'-(N-4-fluorobenzoyl)-(N,N-dimethylethylenediamino)propyl]-3-benzylquinazolin-4-one.

A stock solution of compound 5 (1.822 g, 5.0 mmol) was prepared in HPLC grade CHCl$_3$ (0.5 mL). A stock solution of p-fluorobenzoyl chloride (160.2 mg, 1 mmol) in HPLC grade 1,2-dichloroethane (2.0 mL) was prepared in a 2.0 mL volumetric flask. A third solution of triethylamine (2.0 mL of 0.5 M) was prepared in HPLC grade 1,2-dichlorethane. A 100 μL aliquot of each solution was pipetted into a glass reaction vessel using a Beckman Biomet 2000 automated liquid dispenser. The reaction mixture was shaken using a mechanical shaker, sonicated in an ultrasonic water bath, and then incubated overnight at room temperature. The mixture was diluted in CHCl$_3$ (300 μL) and washed with 5% aqueous NaHCO$_3$ and water. The solvent was removed in vacuo to provide compound 6 (65%). The purity of the compound was analyzed by TLC eluted with CH$_2$Cl$_2$-ethanol-concentrated aqueous NH$_3$, 100:10:1.

Example 2

Figure 3:
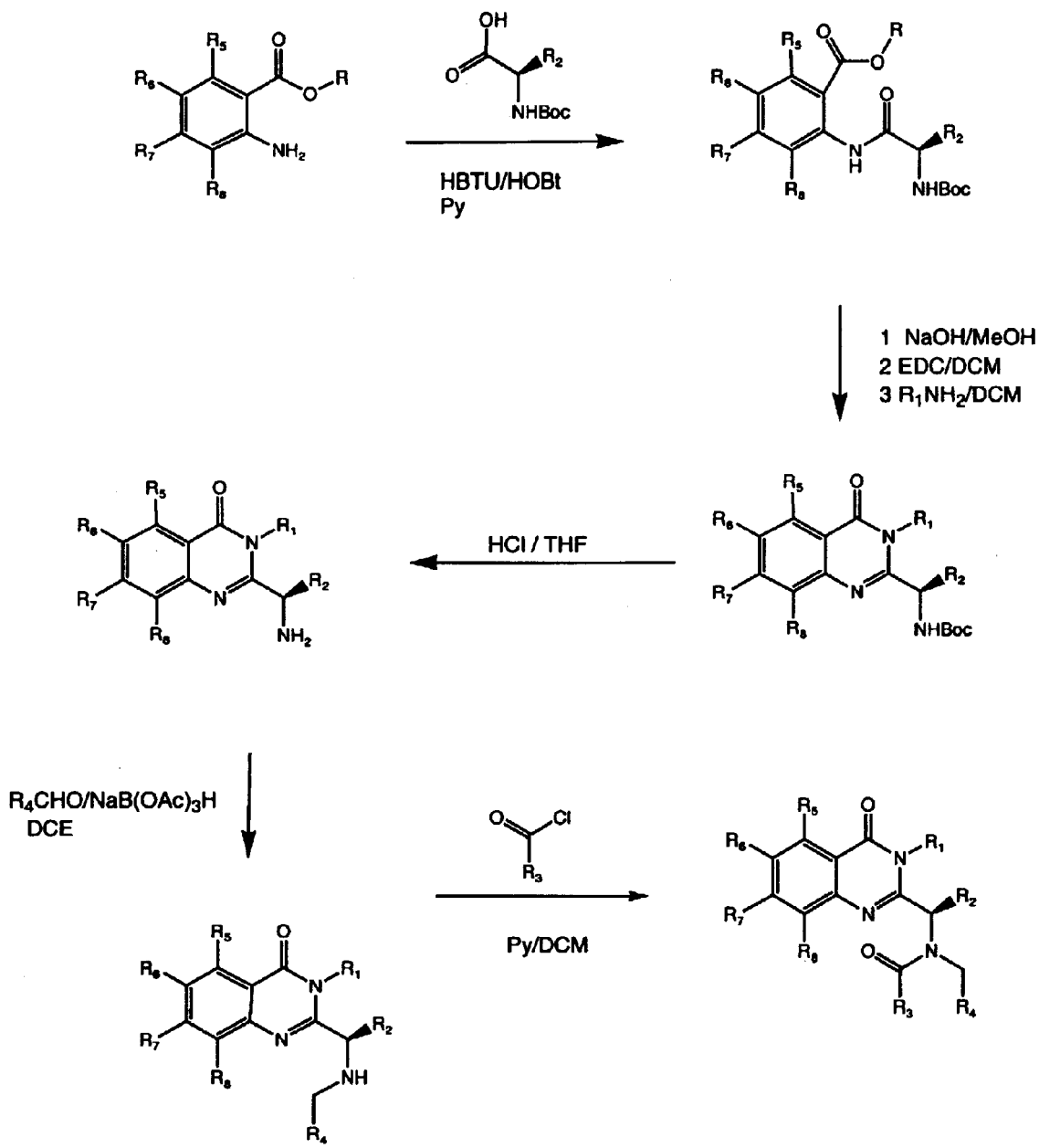
FIG. 3 depicts a synthetic route to substantially pure single enantiomers.

The following two compounds were synthesized as single enantiomers by the route shown in FIG. 3.

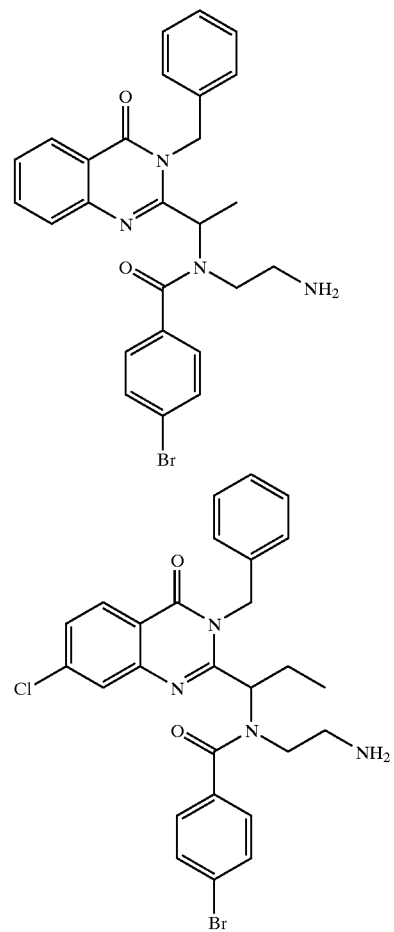

Example 3

Racemization Method

Figure 4:
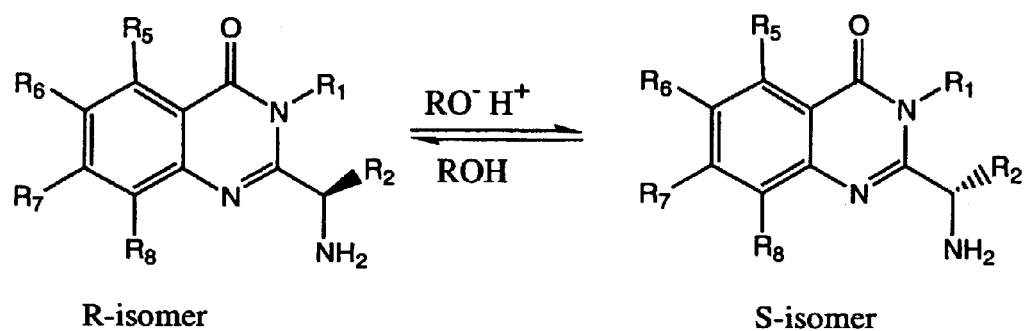
FIG. 4 depicts a method for the racemization of quinazolinone derivatives according to one embodiment of the invention.

The S-isomer of the compound shown in FIG. 4, wherein R$_1$ is benzyl; R$_2$ is isopropyl; R$_5$, R$_6$, and R$_8$ are hydrogen; and R$_7$ is chloro, (490 mg, 1.44 mmol) and sodium ethoxide (0.535 mL of a 21% by weight solution in denatured alcohol containing 5% toluene; 1.64 mmol) were dissolved in abs. ethanol (2.5 mL) and heated at reflux for 36 h. After completion of the reaction, the solvent was evaporated under reduced pressure. The residue was dissolved in dichloromethane and washed with 2N aq. HCl solution which was added dropwise until the solution had a pH of about 7. The organic layer was dried over Na$_2$SO$_4$ and evaporated to dryness under reduced pressure. The remaining product (478 mg, 86% pure by NMR) comprised a 1:1.1 mixture of the R- and S-isomers as shown by chiral liquid chromatography.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A method for the racemization of an enantiomer, or an enantiomerically enriched mixture of a compound of formula,

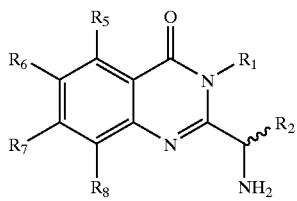

Formula II wherein said method comprises the steps of:
contacting said enantiomer or enantiomerically enriched mixture with an alkali alkoxide in a $C_1$–$C_6$ primary alcohol at a selected racemization reaction temperature whereby said enantiomer or enantiomerically enriched mixture is racemized to yield a racemic mixture; and
isolating the racemic mixture,
wherein
$R_1$ is chosen from hydrogen, alkyl, aryl, alkylaryl, heteroaryl, alkylheteroaryl, substituted alkyl, substituted aryl, substituted alkylaryl, substituted heteroaryl, and substituted alkylheteroaryl;
$R_2$ is alkyl, oxaalkyl, aryl, alkylaryl, heteroaryl, alkylheteroaryl, substituted alkyl, substituted aryl, substituted alkylaryl, substituted heteroaryl, and substituted alkylheteroaryl; and
$R_5$, $R_6$, $R_7$ and $R_8$ are independently chosen from hydrogen, alkyl, alkoxy, halogen, fluoroalkyl, nitro, dialkylamino, alkylsulfonyl, alkylsulfonamido, sulfonamidoalkyl, sulfonamidoaryl, alkylthio, carboxyalkyl, carboxamido, aminocarbonyl, aryl and heteroaryl.

2. The method of claim 1, wherein the $C_1$–$C_6$ primary alcohol is methanol or ethanol.

3. The method of claim 2, wherein the $C_1$–$C_6$ primary alcohol is ethanol.

4. The method of claim 1, wherein the alkali alkoxide is a sodium or potassium alkoxide.

5. The method of claim 1, wherein the alkali alkoxide is sodium ethoxide.

6. The method of claim 1, wherein the racemization reaction temperature is less than 200° C.

7. The method of claim 1, wherein the racemization reaction temperature is less than 100° C.

8. The method of claim 1, wherein the racemization reaction temperature is at the boiling point of the reaction mixture.

9. The method of claim 1, further comprising the step of subjecting the racemic mixture to an optical resolution process whereby the racemic mixture is separated into its corresponding stereoisomers.

10. The method of claim 1, wherein the enantiomer has an R-configuration.

11. The method of claim 1, wherein the enantiomer has an S-configuration.

12. The method of claim 1, wherein the alkali alkoxide is derived from an alkali metal and a $C_1$–$C_6$ primary alcohol.

* * * * *